(12) United States Patent
Li et al.

(10) Patent No.: US 12,402,776 B2
(45) Date of Patent: Sep. 2, 2025

(54) IMAGING CATHETER AND IMAGING DEVICE

(71) Applicant: MICRO-TECH (NANJING) CO., LTD., Jiangsu (CN)

(72) Inventors: Xiaochun Li, Jiangsu (CN); Mingxun Guan, Jiangsu (CN); Duangui Gao, Jiangsu (CN)

(73) Assignee: MICRO-TECH (NANJING) CO., LTD., Nanjing (CN)

( * ) Notice: Subject to any disclaimer, the term of this patent is extended or adjusted under 35 U.S.C. 154(b) by 558 days.

(21) Appl. No.: 17/820,244

(22) Filed: Aug. 16, 2022

(65) Prior Publication Data
US 2022/0386853 A1    Dec. 8, 2022

Related U.S. Application Data

(63) Continuation of application No. PCT/CN2021/075596, filed on Feb. 5, 2021.

(30) Foreign Application Priority Data

Mar. 4, 2020  (CN) .......................... 202010144400.5

(51) Int. Cl.
*A61B 1/00* (2006.01)
*A61B 1/012* (2006.01)
(Continued)

(52) U.S. Cl.
CPC ...... *A61B 1/00071* (2013.01); *A61B 1/00114* (2013.01); *A61B 1/00124* (2013.01);
(Continued)

(58) Field of Classification Search
CPC ............ A61B 1/00071; A61B 1/00114; A61B 1/00124; A61B 1/012; A61B 1/04;
(Continued)

(56) References Cited

U.S. PATENT DOCUMENTS 4,788,967 A * 12/1988  Ueda .................. A61B 1/00089
                                                           385/119
2005/0038320 A1   2/2005  Hartwick
(Continued)

FOREIGN PATENT DOCUMENTS

CN   203000885 U   6/2013
CN   103491845 A   1/2014
(Continued)

OTHER PUBLICATIONS

The extended European search report received in the corresponding European application 21764987.0, mailed Jun. 15, 203, 6 pages.
(Continued)

*Primary Examiner* — Aaron B Fairchild
(74) *Attorney, Agent, or Firm* — Kilpatrick Townsend & Stockton LLP

(57) ABSTRACT

An imaging catheter and an imaging device relate to a technical field of medical devices. The imaging catheter includes a metal wire tube, a tip and a retaining ring. A metal wire exposed at one end of the metal wire tube forms a conductive end, which is electrically connected with the tip so as to allow the metal wire to be used as a conductive medium to lead static electricity out of the tip, thereby reducing effects of static electricity on a photographing assembly at the tip, and the harm of static electricity to human body. The retaining ring covers the conductive end and is connected with the tip, so as to make the metal wire tube fixedly connected with the tip.

14 Claims, 4 Drawing Sheets

(51) Int. Cl.
*A61B 1/04* (2006.01)
*A61B 1/05* (2006.01)

(52) U.S. Cl.
CPC ............... *A61B 1/012* (2013.01); *A61B 1/04* (2013.01); *A61B 1/05* (2013.01)

(58) Field of Classification Search
CPC ......... A61B 1/05; A61B 1/0008; A61B 1/005; A61B 1/0055
See application file for complete search history.

(56) References Cited

U.S. PATENT DOCUMENTS

| | | | |
|---|---|---|---|
| 2008/0051634 A1* | 2/2008 | Yamashita | A61B 1/00071 600/153 |
| 2010/0307630 A1 | 12/2010 | Kaneko et al. | |
| 2012/0271108 A1* | 10/2012 | Hoshino | A61B 1/00091 600/139 |
| 2020/0015664 A1 | 1/2020 | Hatase et al. | |

FOREIGN PATENT DOCUMENTS

| | | | | |
|---|---|---|---|---|
| CN | 104964104 A | 10/2015 | | |
| CN | 107135345 A | 9/2017 | | |
| CN | 209377530 U | 9/2019 | | |
| CN | 110355452 A | 10/2019 | | |
| CN | 211834307 U | 11/2020 | | |
| JP | 2010-005269 A | * | 6/2008 | ............... A61B 1/00 |
| JP | 2010269014 A | 12/2010 | | |
| JP | 2012500102 A | 1/2012 | | |
| JP | 2015039410 A | 3/2015 | | |
| JP | 2017213317 A | 12/2017 | | |

OTHER PUBLICATIONS

Notice of Reasons of Refusal received in the corresponding Japanese application 2022-550235, mailed Jun. 27, 2023.
Office Action of Chinese Patent Application No. 202010144400.5 Mailed Jul. 8, 2024.
International Search Report and Written Opinion mailed in International Application PCT/CN2021/075596 on Apr. 25, 2021.

* cited by examiner

IMAGING CATHETER AND IMAGING DEVICE

CROSS-REFERENCE TO RELATED APPLICATIONS

This application is a continuation of International Application No. PCT/CN2021/075596, filed on Feb. 5, 2021, which claims priority to Chinese Patent Application No. 2020101444005, filed on Mar. 4, 2020. The disclosures of the aforementioned applications are hereby incorporated by reference in their entireties.

TECHNICAL FIELD

The present disclosure relates to the technical field of medical instruments, and in particular, to an imaging catheter and an imaging device.

BACKGROUND

During treatment, in order to better know about the situation inside the human body, a photographing assembly at a distal end of the imaging device can be extended into the human body, so as to image the internal condition of the human body on a screen for checking. For example, the photographing assembly that comes with a choledochoscope system can be used to directly observe pathological changes and stones in a biliary tract, which greatly improves the accuracy of the treatment of biliary diseases.

In the case that the imaging device works with the photographing assembly, since the photographing assembly is an electronic component, which is highly susceptible to static electricity, the problem of unstable picture occurs, thus affecting the imaging result. At present, in order to improve the stability of picture display of the photographing assembly, for some imaging devices, a ground lead is provided at the photographing assembly of the imaging device to lead out static electricity. However, the newly added ground lead occupies limited space and leads to a complicated structure of the imaging device.

SUMMARY

A purpose of the present disclosure includes, for example, providing an imaging catheter, which is capable of saving space while leading out static electricity and/or reducing the effects of static electricity on an imaged picture.

The purpose of the present disclosure further includes, providing an imaging device, which is capable of saving space while leading out static electricity and/or reducing the effects of static electricity on an imaged picture.

Embodiments of the present disclosure may be implemented as follows.

The embodiments of the present disclosure provide an imaging catheter, including a metal wire tube, a tip and a retaining ring; a metal wire exposed at one end of the metal wire tube form a conductive end; and the retaining ring wraps the conductive end and is connected with the tip, so as to make the conductive end electrically connected with the tip.

Optionally, the conductive end is electrically connected with the tip through the retaining ring.

Optionally, a distal end of the conductive end includes a plurality of metal wire tips arranged in sequence along a circumferential direction of the metal wire tube, and the plurality of metal wire tips are all electrically connected with the retaining ring.

Optionally, the conductive end is in contact with the tip, so as to make the conductive end electrically connected with the tip.

Optionally, the metal wire tube and the tip are arranged side by side, and the retaining ring is sleeved at a proximal end of the tip.

Optionally, an outer wall of the tip includes a first peripheral surface and a second peripheral surface that are arranged in sequence along an axial direction of the tip, and a radial dimension of the first peripheral surface is smaller than that of the second peripheral surface; and an inner wall of the retaining ring is matched with the first peripheral surface.

Optionally, the outer wall further includes a stepped surface, two ends of the stepped surface are respectively connected with the first peripheral surface and the second peripheral surface, and the stepped surface is configured to limit a distal end of the retaining ring.

Optionally, the surface of step is disposed along a radial direction of the tip.

Optionally, the metal wire tube includes an insulating tube and a metal wire; part of the metal wire is located inside the insulating tube and part of the metal wire protrudes beyond a distal end of the insulating tube to form the conductive end.

Optionally, the insulating tube is thermoformed on the metal wire, so as to cover part of the metal wire.

Optionally, the insulating tube is sleeved on a proximal end of the retaining ring.

Optionally, the imaging catheter further includes a multi-cavity tube, which is sleeved with the metal wire tube.

Optionally, the multi-cavity tube has a one-piece structure.

Optionally, the metal wire tube is further provided with an export end, the export end being electrically connected with the conductive end and configured to be grounded.

Optionally, the metal wire tube further includes a lead, one end of the lead being electrically connected with the conductive end and the other end of the lead being configured to be grounded so as to form the export end.

An embodiment of the present disclosure further provides an imaging device, including a photographing assembly and any of the above imaging catheters, the photographing assembly being mounted in the tip of the imaging catheter.

The imaging catheter and imaging device of the embodiments of the present disclosure include the following beneficial effects, for example.

Embodiments of the present disclosure provide an imaging catheter, including a metal wire tube, a tip, and a retaining ring. A metal wire exposed at one end of the metal wire tube forms a conductive end, which is electrically connected with the tip, so that the metal wire may be used as a conductive medium to lead the static electricity out from the tip, thereby reducing the effects of static electricity on the photographing assembly at the tip, and reducing the harm of static electricity to the human body. At the same time, since it is not necessary to additionally arrange a ground lead at the photographing assembly, the space is effectively saved. The retaining ring covers the conductive end and is connected to the tip, so as to make the metal wire tube fixedly connected with the tip. In addition, since the conductive end is an exposed metal wire, covering of the conductive end by the retaining ring can effectively avoid the human body damage caused by a sharp part formed by the metal wire, thereby having a good effect for use.

Embodiments of the present disclosure further provide an imaging device including the above imaging catheter. Since the imaging device includes the imaging catheter, it also has the beneficial effects of reducing the effects of static electricity on the photographing assembly at the tip while having a good effect for use.

BRIEF DESCRIPTION OF THE DRAWINGS

In order to illustrate the technical solutions in the embodiments of the present disclosure more clearly, the accompanying drawings that are needed in the description of the embodiments will be introduced briefly below. It should be understood that the following drawings only illustrate some embodiments of the present disclosure and cannot be considered as a limitation on its scope. For those of ordinary skill in the art, other related drawings may be obtained according to these drawings without paying a creative labor.

REFERENCE NUMERALS

Figure 1:
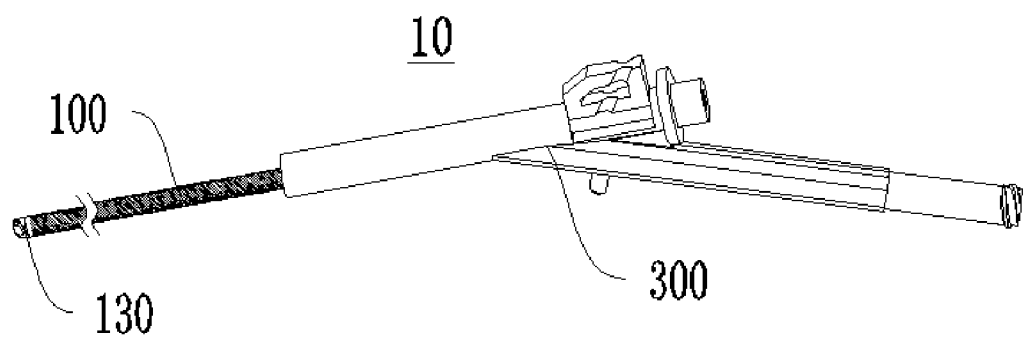
FIG. 1 is a schematic diagram of an overall structure of an imaging device provided by an embodiment of the present disclosure.

10, imaging device; 100, imaging catheter; 110, metal wire tube; 111, metal mesh; 112, conductive end; 113, insulating tube; 114, lead; 115, export end; 120, multi-cavity tube; 121, photographing channel; 122, working channel; 123, leading wire channel; 124, injection channel; 130, tip; 131, first peripheral surface; 132, stepped surface; 133, second peripheral surface; 134, photographing hole; 135, working hole; 136, leading wire hole; 137, injection hole; 140, retaining ring; 200, photographing assembly; 210, lens; 220, transmission line; 300, handle.

DESCRIPTION OF EMBODIMENTS

In order to make the purpose, technical solutions and advantages of the embodiments of the present disclosure clearer, the technical solutions in the embodiments of the present disclosure will be clearly and completely described below in conjunction with the accompanying drawings in the embodiments of the present disclosure. Apparently, the described embodiments are a part of the embodiments of the present disclosure, rather than all of the embodiments. In general, the components of the embodiments of the present disclosure described and illustrated in the drawings herein may be arranged and designed in a variety of different configurations.

Therefore, the following detailed description of the embodiments of the present disclosure provided in the accompanying drawings is not intended to limit the scope of the disclosure as claimed, but is merely representative of selected embodiments of the present disclosure. Based on the embodiments in the present disclosure, all other embodiments obtained by those of ordinary skill in the art without paying creative work shall fall within the scope of protection of the present disclosure.

It should be noted that similar numerals and letters refer to similar items in the following drawings. Therefore, once some item is defined in one drawing, it is not required to be further defined and explained in subsequent drawings.

In the description of the present disclosure, it should be noted that in the case that the orientation or positional relationship is indicated by the terms such as "upper", "lower", "inner" and/or "outer", it is based on the orientation or positional relationship shown in the accompanying drawings or is the orientation or position relationship that is customarily placed when the product of the disclosure is used, which is only for ease of describing the present disclosure and simplifying the description, rather than indicating or implying that the referred device or element must have a particular orientation or must be constructed and operated in a particular orientation. Therefore, it should not be construed as a limitation of the present disclosure.

In addition, the terms "first" and/or "second" and the like are only used for distinguishing description, and should not be construed as indicating or implying relative importance.

It should be noted that the features of the embodiments of the present disclosure may be combined with each other in the case of no conflict.

Figure 2:
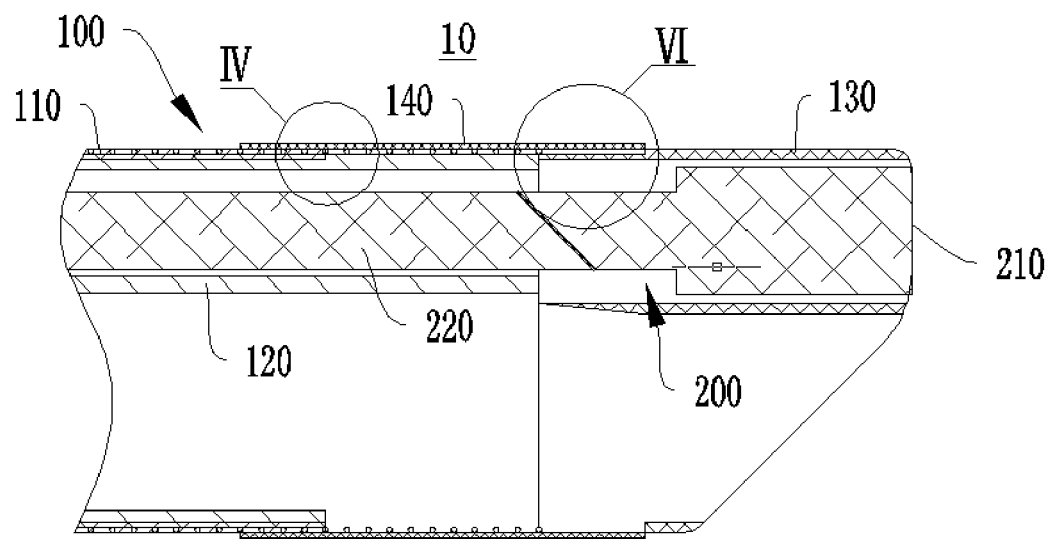
FIG. 2 is a schematic cross-sectional diagram of a partial structure of an imaging device provided by an embodiment of the present disclosure from a first perspective.
Figure 3:
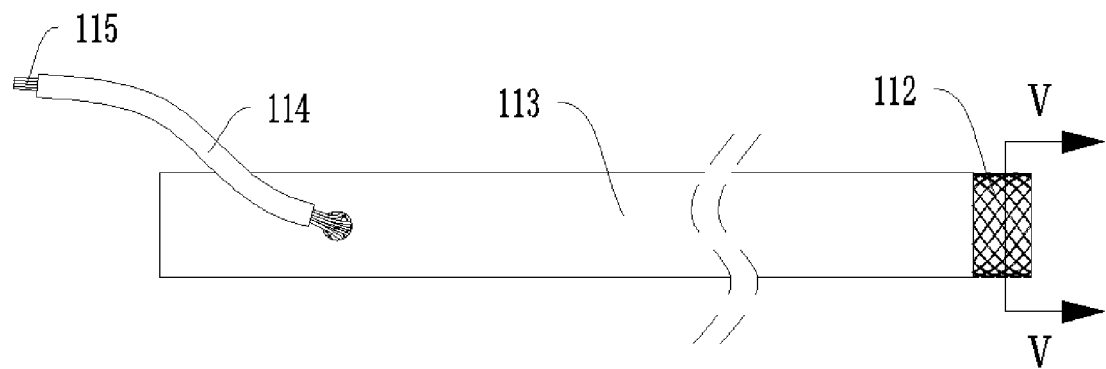
FIG. 3 is a schematic structural diagram of a metal wire tube in an imaging device provided by an embodiment of the present disclosure.

FIG. 1 is a schematic diagram of an overall structure of an imaging device 10 provided by an embodiment of the present disclosure; FIG. 2 is a schematic cross-sectional diagram of a partial structure of an imaging device 10 provided by an embodiment of the present disclosure from a first perspective; FIG. 3 is a schematic structural diagram of a metal wire tube 110 in an imaging device 10 provided by an embodiment of the present disclosure. Referring to FIG. 1, FIG. 2 and FIG. 3, this embodiment provides an imaging catheter 100, and accordingly, provides an imaging device 10.

The imaging device 10 includes an imaging catheter 100 and a photographing assembly 200 provided in the imaging catheter 100.

Specifically, the imaging catheter 100 includes a metal wire tube 110, a tip 130 and a retaining ring 140. A metal wire exposed at one end of the metal wire tube 110 forms a conductive end 112, which is electrically connected with the tip 130, so that the metal wire inside the metal wire tube 110 can be used as a conductive medium to lead out the static electricity at the tip 130, thereby reducing the effects of static electricity on the photographing assembly 200 at the tip 130, and reducing the harm of static electricity to the human body; at the same time, since a ground lead is not required to be disposed at the photographing assembly 200, a space is effectively saved. The retaining ring 140 covers the conductive end 112 and is connected with the tip 130, so that the metal wire tube 110 is connected and fixed to the tip 130. Furthermore, since the conductive end 112 is a metal wire that is exposed, covering of the conductive end 112 by the retaining ring 140 may effectively prevent a sharp part formed by the metal wire from damaging the human body, having a better using effect.

The photographing assembly 200 includes a transmission line 220 and a lens 210 connected with a distal end of the transmission line 220. The lens 210 is fixed in a channel inside the tip 130, and the transmission line 220 is arranged in the metal wire tube 110. When in use, the lens 210 of the photographing assembly 200 is fed by the imaging catheter 100 to a location that is required to be directly observed for imaging, to identify pathological changes and ensure the accuracy of treatment. At the same time, the imaging device 10 further includes a handle 300, which is located at one end of the metal wire tube 110 away from the tip 130. When in use, the imaging catheter 100 and photographing assembly 200 are subjected to an operation via the handle 300.

The imaging catheter 100 provided in this embodiment is further described below.

Figure 4:
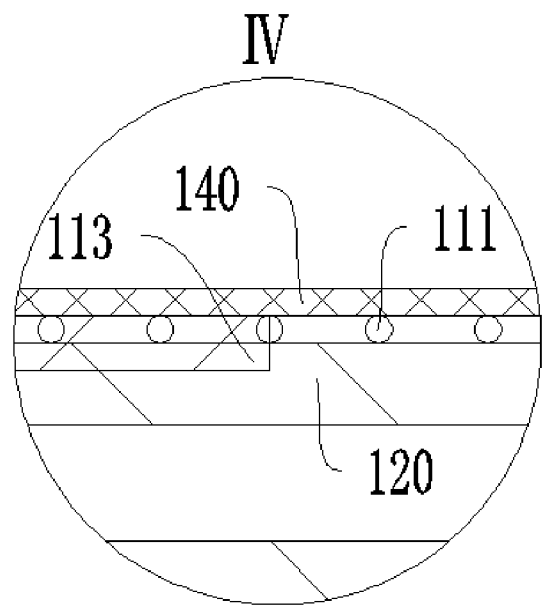
FIG. 4 is an enlarged schematic diagram of a partial structure at IV in FIG. 2.
Figure 5:
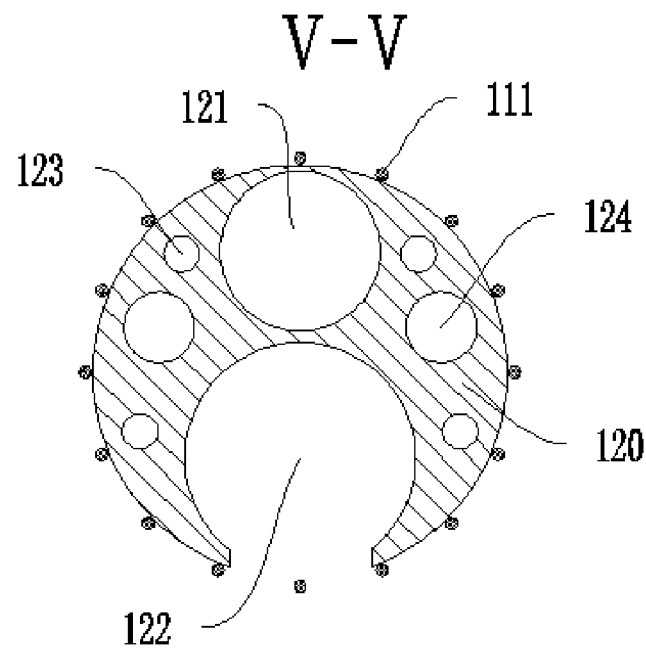
FIG. 5 is a cross-sectional diagram taken along line V-V in FIG. 3.

FIG. 4 is an enlarged schematic diagram of a partial structure at IV in FIG. 2; and FIG. 5 is a schematic cross-sectional diagram at V-V in FIG. 3. Referring to FIG. 1 to FIG. 5, in this embodiment, the metal wire tube 110 includes a metal wire and an insulating tube 113; part of the metal wire is located in the insulating tube 113 and part of the metal wire protrudes out of a distal end of the insulating tube 113, so that part of the metal wire is exposed outside the distal end of the insulating tube 113 to form the conductive end 112. The conductive end 112 is electrically connected with the tip 130, so that the static electricity at the tip 130 may be conducted via the conductive end 112 to the metal wire that is located in the insulating tube 113. Optionally, the insulating tube 113 is subjected to thermoplastic forming on the metal wire, so as to cover part of the metal wire.

It should be noted that, in this embodiment, a "proximal end" of each component in the imaging catheter 100 refers to an end of each component that is close to the handle 300, and a "distal end" of each component in the imaging catheter 100 refers to an end of each component away from the handle 300. For example, the distal end of the metal wire tube 110 is the end of the metal wire tube 110 away from the handle 300, that is, the end of the metal wire tube 110 close to the tip 130; and the proximal end of the tip 130 is the end of the tip 130 close to the handle 300, that is, the end of the tip 130 close to the metal wire tube 110.

Referring to FIG. 3, in this embodiment, the metal wire tube 110 also has an export end 115, which is electrically connected with the conductive end 112 and is configured to be grounded, thereby leading the static electricity of the tip 130 into the conductive end 112 and then to be guided to the export end 115, so as to form a conductive path to lead out the static electricity. Specifically, the export end 115 is electrically connected with a grounding circuit board (not shown) in the handle 300.

Optionally, the metal wire tube 110 further includes a lead 114. The lead 114 is pre-embedded in the proximal end of the metal wire, one end of the lead 114 being electrically connected with the metal wire, and the other end being connected with the grounding circuit board of the handle 300 for grounding. That is, the end of the lead 114 away from the metal wire is the export end 115 of the metal wire tube 110, so as to make the metal wire be used as an intermediate conductive medium to form a complete conductive path, which helps to save space and simplify a structure.

It should be noted that in this embodiment, the metal wire tube 110 includes the lead 114, and the export end 115 of the metal wire tube 110 is an end of the lead 114 that is connected to the grounding circuit board of the handle 300. It can be understood that in other embodiments, the export end 115 may also be formed in other ways as required. For example, the insulating tube 113 at the proximal end of the metal wire tube 110 is peeled off to expose a metal mesh 111 at this position, thereby allowing the metal wire exposed at the proximal end of the metal mesh 111 to form the export end 115.

Figure 6:
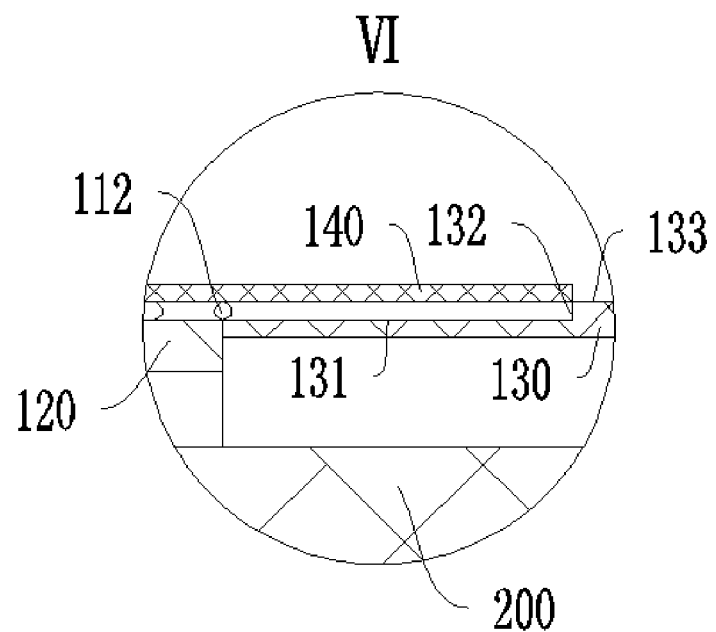
FIG. 6 is an enlarged schematic diagram of a partial structure at VI in FIG. 2.
Figure 7:
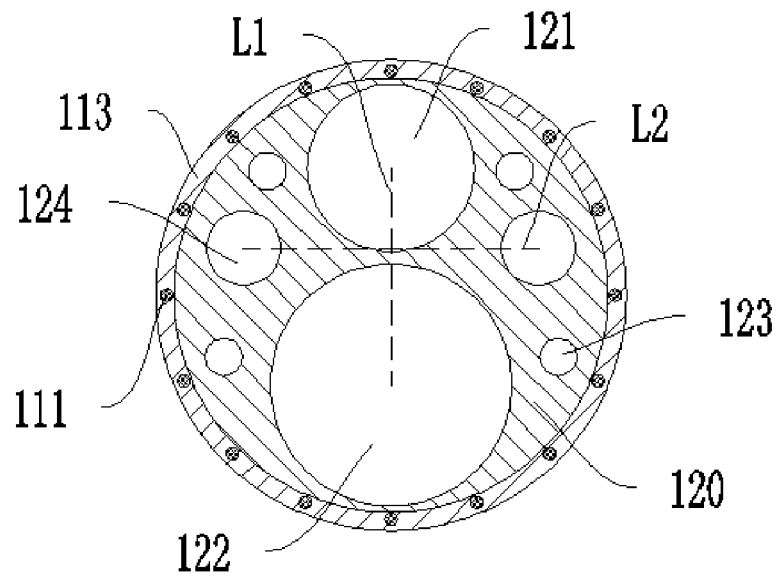
FIG. 7 is a schematic cross-sectional structural diagram of an imaging catheter provided by an embodiment of the present disclosure from a second perspective.

FIG. 6 is an enlarged schematic diagram of a partial structure at VI in FIG. 2; FIG. 7 is a schematic cross-sectional structural diagram of an imaging catheter 100 provided by the embodiment from a second perspective. Referring to FIG. 2, FIG. 6 and FIG. 7, in this embodiment, the imaging catheter 100 further includes a multi-cavity tube 120 disposed in the metal wire tube 110.

Specifically, in the process of production and installation, first, a multi-strand metal wire is used to form a tubular metal mesh 111 by weaving outside of the multi-cavity tube 120, and an end surface of a distal end of the tubular metal mesh 111 is flush with that of a distal end of the multi-cavity tube 120. A single-cavity tube made of insulating material is then sleeved outside the metal mesh 111, and is subsequently melted to coat the metal mesh 111 by hot melting, so as to form a tubular member by which the metal mesh 111 is coated after cooling, that is, the insulating tube 113 is thermoformed. At this point, the metal mesh 111 is entirely wrapped inside the insulating tube 113; at the same time, the formed insulating tube 113 is tightly adhered to the multi-cavity tube 120 by means of hot melting, which has a robust connection and high reliably. Finally, the insulating tube 113 at the distal end of the metal mesh 111 is peeled off to make the metal wire that is located at the distal end of the metal mesh 111 exposed outside of the insulating tube 113, so as to form the conductive end 112, and the conductive end 112 is electrically connected with the tip 130 to lead out the static electricity at the tip 130. It can be understood that, in other embodiments, other manufacturing methods may also be used; for example, a metal wire tube 110 is prefabricated, the multi-cavity tube 120 is then allowed to penetrate through the metal wire tube 110, and finally, the metal wire tube 110 is connected with the multi-cavity tube 120 by means of bonding or the like. Moreover, in this embodiment, multi-strand metal wire is woven to form a mesh. It can be understood that in some other embodiments, it is also possible to arrange the multi-strand metal wire at intervals along a circumferential direction of the multi-cavity tube 120 as required.

It should be noted that in this embodiment, the conductive end 112 is formed by peeling off the insulating tube 113 at the distal end of the metal mesh 111 to expose the metal wire. It can be understood that in this embodiment, the conductive end 112 may also be formed in other ways as required. For example, a single-cavity tube with a length smaller than the metal mesh 111 is selected to be sleeved outside the metal mesh 111, so that one end of the metal mesh 111 protrudes out of the single-cavity tube and is then exposed outside the single-cavity tube; after hot-melting of the single-cavity tube, the metal wire that is located at one end of the metal mesh 111 and exposed outside the single-cavity tube naturally protrudes out of the insulating tube 113 formed, thereby forming the conductive end 112. At the same time, it may also be understood that in other embodiments, the insulating tube 113 may also be formed by other ways, such as jetting and extrusion.

By arranging the metal wire tube 110 outside the multi-cavity tube 120, the strength of the multi-cavity tube 120 may be effectively enhanced, so that the imaging catheter 100 has a good pushing performance, and in case of passing through a curved channel, the damage of the multi-cavity tube 120 is obviated and the degree of deformation of the cross section of the multi-cavity tube 120 may be reduced. In other words, when the multi-cavity tube 120 passes through the curved channel, the shape of each cross section at a bend may still remain substantially circular; therefore, it may be ensured that channels in the multi-cavity tube 120 are not deformed. It should be noted that in this embodiment, the "cross section" refers to a plane which is cut from a plane perpendicular to the axis of the multi-cavity tube 120.

Optionally, the multi-cavity tube 120 has a one-piece structure, that is, the multi-cavity tube 120 has a complete one-piece tubular structure, which may be integrally molded by injection molding or pouring, etc., or be integrally formed by bonding or welding, etc. It may be understood that in other embodiments, the multi-cavity tube 120 may also be set to be formed by splicing multiple materials as required.

Referring to FIG. 5 and FIG. 7, the multi-cavity tube 120 has a plurality of channels, which are divided into a photographing channel 121, a working channel 122, a leading wire channel 123 and an injection channel 124, according to respective functions.

Specifically, many channels in the multi-cavity tube 120 are all circular channels. The photographing channel 121 and the working channel 122 are arranged at intervals in the middle of the multi-cavity tube 120 along a radial direction of the multi-cavity tube 120; that is, the connection line formed by the center of the photographing channel 121 and the center of the working channel 122 passes through the center of the multi-cavity tube 120, where the connection line is a first connection line L1. The radial dimension of the photographing cavity 121 is smaller than that of the working channel 122. There are two injection channels 124, which are respectively located on both sides of the connection line L1, and the centers of the two injection channels 124 are connected to form a connection line that is a second connection line L2. At the same time, in order to facilitate the arrangement of the two injection channels 124, ensure the injection volume and facilitate the injection operation, the intersection between the second connection line L2 and the first connection line L1 is located between the photographing channel 121 and the working channel 122. There are four leading wire channels 123, which are oppositely arranged on both side of the first connection line L1 in a group of two. That is, two of the four leading wire channels 123 are located on one side of the first connection line L1, and the other two are located on the other side of the first connection line L1. At the same time, the two leading wire channels 123 that are located on the same side of the first connection line L1 are distributed on two sides of the second connection line L2, respectively.

It should be noted that there is no limitation on the number, location and/or size of the channel in the multi-cavity tube 120 herein. It can be understood that in other embodiments, the channel may also be provided as required, for example, the number of the leading wire channels 123 may be set to two, etc.

Figure 8:
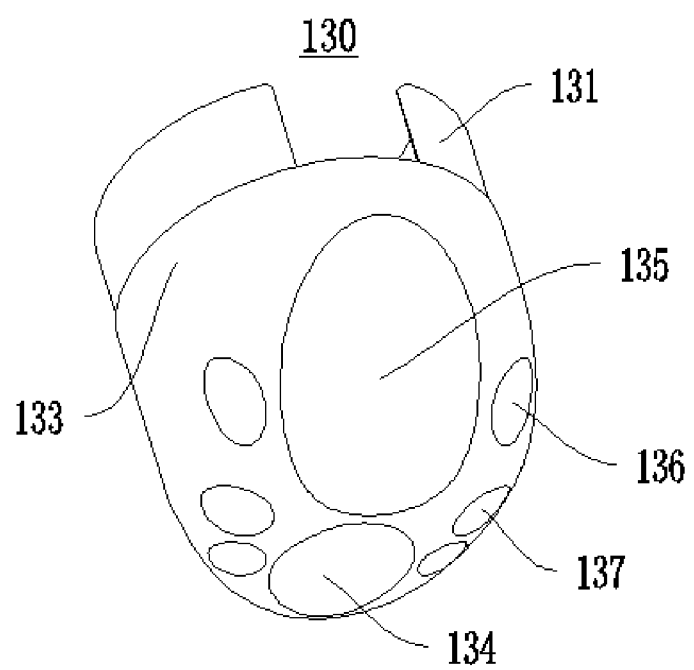
FIG. 8 is a schematic structural diagram of a tip in an imaging catheter provided by an embodiment of the present disclosure.

FIG. 8 is a schematic structural diagram of a tip 130 in an imaging catheter 100 provided by this embodiment. Referring to FIG. 2 and FIG. 8, the tip 130 of the imaging catheter 100 is located at the distal end of the imaging catheter 100. In this embodiment, the tip 130 is made of medical grade metal materials. Optionally, the material of the tip 130 is medical grade 304-type stainless steel. It can be understood that in some other embodiments, the tip 130 may also be made of other medical grade metal materials or rigid plastic materials as required, such as PEEK (polyetheretherketone).

Referring to FIG. 5, FIG. 7 and FIG. 8, the tip 130 is provided with a plurality of through-holes, which are each arranged to penetrate through the tip 130 along an axial direction of the tip 130. These through-holes are provided in one-to-one correspondence with the plurality of channels in the multi-cavity tube 120. Correspondingly, the plurality of through-holes at the tip 130 are respectively divided into an injection hole 137, a leading wire hole 136, a working hole 135 and a photographing hole 134 according to respective functions.

The injection hole 137 is provided to correspond to the injection channel 124; that is, the injection hole 137 is communicated with the injection channel 124, so that liquid can be injected through the injection channel 124 and the injection hole 137. For example, during the imaging process of the photographing assembly 200, if the lens 210 of the photographing assembly 200 is blocked due to bleeding, physiological saline or the like may be injected through the injection channel 124 and the injection hole 137 to flush the lens 210. Specifically, the number of injection holes 137 is set to two, and two injection holes 137 are provided in one-to-one correspondence with the two injection channels 124.

The leading wire hole 136 is arranged to correspond to the leading wire channel 123; that is, the leading wire channel 123 is communicated with the leading wire hole 136 for allow the leading wire to pass through. Specifically, the number of the leading wire hole 136 is set to four, and four leading wire holes 136 are provided in one-to-one correspondence with four leading wire channels 123.

The working hole 135 is arranged to correspond to the working channel 122; that is, the working channel 122 is communicated with the working hole 135 to meet the operation and treatment requirements. For example, some operation instruments are inserted into the human body through the working channel 122 and the working hole 135.

The photographing hole 134 corresponds to the photographing channel 121; that is, the photographing hole 134 is communicated with the photographing channel 121. The lens 210 of the photographing assembly 200 is located in the photographing hole 134, and acquires human body images through the opening of the photographing hole 134 which is disposed at the distal end of the tip 130. The transmission line 220 of the photographing assembly 200 is arranged to pass through the photographing channel 121, the distal end of the transmission line 220 is connected with the lens 210, and the proximal end of the transmission line 220 extends to the handle 300 and is connected with a display device (not shown) to output an imaged picture.

It should be noted that the number, location, size and function of the plurality of through-holes in the tip 130 are not limited herein. It can be understood that in other embodiments, it may also be set as required. For example, only some of the injection holes 137, the leading wire holes 136 and the working holes 135 are selected to be disposed in the tip 130, as required; or if there are two leading wire channels 123 of the multi-cavity tube 120, the number of leading wire holes 136 is accordingly set to two.

Referring to FIG. 1 to FIG. 4, in this embodiment, the imaging catheter 100 further includes a retaining ring 140, which is sleeved on the conductive end 112 and connected with the tip 130, so as to fix the metal wire tube 110 with the tip 130. Moreover, the retaining ring 140 wraps the end of the conductive end 112, so that a sharp structure formed by the bare metal wire end which forms the conductive end 112 is wrapped in the retaining ring 140, thereby preventing the human body from being damaged by such sharp structure.

Along the axial direction of the imaging catheter 100, the metal wire tube 110 is arranged side by side with the tip 130; that is, the end face of the distal end of the metal wire tube 110 and the end face of the proximal end of the tip 130 are matched with each other in a butted manner or are arranged at a small distance apart; moreover, in the case that the end face of the distal end of the metal wire catheter 110 and the end face of the proximal end of the tip 130 are arranged at intervals, the metal wire tube 110 and the tip 130 are arranged at intervals. That is, there is no nesting relationship between the metal wire tube 110 and the tip 130. The proximal end of the retaining ring 140 is sleeved on the metal wire tube 110, and the distal end of the retaining ring 140 is sleeved on the tip 130, so that the metal wire tube 110 and the tip 130 are fixed to each other.

Further, the retaining ring 140 completely wraps the conductive end 112, and the proximal end of the retaining ring 140 is extended and sleeved outside the insulating tube 113, so the wire exposed outside the insulating tube 113 are completely covered by the retaining ring 140, which prevents the wire from being exposed and affecting its use.

In this embodiment, since the end face of the distal end of the metal mesh 111 formed by the wire is flush with that of the distal end of the multi-cavity tube 120 and there is no nesting relationship between the metal wire tube 110 and the tip 130, the retaining ring 140 is provided with a conductive portion, so as to electrically connect the conductive end 112 and the tip 130. At the same time, the conductive portion is electrically connected with each of the conductive end 112 and the tip 130, thereby realizing the electrical connection between the conductive end 112 and the tip 130 via the conductive portion. That is, the conductive end 112 is electrically connected with the tip 130 through the retaining ring 140.

It should be noted that in this embodiment, the retaining ring 140 is used as an intermediate conductive medium between the conductive end 112 and the tip 130, and the conductive end 112 is electrically connected with the tip 130 through the retaining ring 140. It can be understood that, in some other embodiments, the electrical connection of the conductive end 112 with the tip 130 may be realized through contact between the conductive end 112 and the tip 130, as required. For example, the distal end of the metal mesh 111 is configured to protrude beyond the multi-cavity tube 120 in the axial direction, so that the conductive end 112 disposed at the distal end of the metal mesh 111 is in contact with the tip 130; alternatively, the proximal end of the tip 130 is sleeved on the conductive end 112, so that an inner peripheral surface of the proximal end of the tip 130 is in contact with the conductive end 112, so as to realize the electrical connection between the conductive end 112 and the tip 130.

Since in the metal wire tube 110, multi-strand metal wires are woven to form a tubular metal mesh 111, the conductive end 112 is a part that is at the distal end of the metal mesh 111 and is exposed outside the insulating tube 113, and so the conductive end 112 is annular. A plurality of metal wire tips are arranged at the distal end of the conductive end 112 along the circumferential direction of the metal wire tube 110, the metal wire tip being an end formed by cutting off the metal wire. The conductive portion in the retaining ring 140 is annular and the plurality of metal wire tips are each electrically connected with the conductive portion, so that all the metal wires may export static electricity from the conductive portion. That is, all metal wires may be used for grounding to lead out the static electricity, so that the grounding effect can be effectively improved and the leading out effect of the static electricity is better.

Optionally, the retaining ring 140 is made of metal material; that is, the whole retaining ring 140 is conductive. In other words, the whole retaining ring 140 may be used as a conductive part to make the conductive end 112 be electrically connected with the tip 130. It can be understood that the specific material of the retaining ring 140 is not limited in this embodiment, as long as it may be used as an intermediate conductive medium to realize electrical connection of the conductive end 112 with the tip 130.

It should be noted that, in this embodiment, the retaining ring 140 is made of metal material, so that the whole retaining ring 140 is conductive. It can be understood that, in some other embodiments, as required, only part of the retaining ring 140 is made of metal material that is conductive. For example, a metal coating is provided at a place where the inner wall of the retaining ring is in contact with the tip 130 and the conductive end 112, so as to electrically connect the conductive end 112 and the tip 130; and an annular conductive portion may be formed, as long as all the metal wires may be electrically connected with the tip 130.

Referring to FIG. 2, FIG. 6 and FIG. 8, in this embodiment, along the axial direction of the tip 130, the outer wall of the tip 130 includes a first peripheral surface 131 and a second peripheral surface 133 that are arranged in sequence, and a radial dimension of the first peripheral surface 131 is smaller than that of the second peripheral surface 133. Specifically, the first peripheral surface 131 is located at the proximal end of the tip 130, and the second peripheral surface 133 is located at the distal end of the tip 130. The inner wall of the retaining ring 140 is matched with the first peripheral surface 131, so that the radial dimension of a connection between the retaining ring 140 and the tip 130 may be effectively reduced, which is convenient to operate the imaging catheter 100 into the human body.

The first peripheral surface 131 is cylindrical surface, and the proximal end of the second peripheral surface 133 is also cylindrical. Meanwhile, the radial dimension of the first peripheral surface 131 is smaller than that of the proximal end of the second peripheral surface 133, so that an outer portion of the tip 130 forms a stepped structure. The tip 130 also includes a stepped surface 132, which is located between the first peripheral surface 131 and the second peripheral surface 133, and two ends of the stepped surface 132 are respectively connected with the first peripheral surface 131 and the second peripheral surface 133. Since the radial dimension of the first peripheral surface 131 is smaller than that of the second peripheral surface 133, the first peripheral surface 131 and the stepped surface 132 are connected to form a notch recessed inward in a radial direction, relative to the second peripheral surface 133, and the distal end of the retaining ring 140 is arranged in this notch. In this embodiment, the retaining ring 140 is connected with the tip 130 by laser welding. Optionally, in some other embodiments, the retaining ring 140 may be connected with the tip 130 in other ways such as gluing; or the distal end of the retaining ring 140 may be pressed against the first peripheral surface 131.

In this embodiment, the notch is formed by performing machining at the cylindrical proximal end of the tip 130. Optionally, in some other embodiments, the tip 130 may also be formed in other ways, for example, it may be integrally formed by powder metallurgy.

At the same time, the end face of the distal end of the retaining ring 140 abuts against the stepped surface 132, so that the retaining ring 140 is limited by the stepped surface 132, so as to ensure that the retaining ring 140 is connected with the tip 130 reliably. Optionally, the surface of step 132 is arranged along a radial direction of the tip 130; that is, the plane where the surface of step 132 is located is perpendicular to the axis of the tip 130, and at the same time, the stepped surface 132 is disposed perpendicular to both the first peripheral surface 131 and the second peripheral surface 133.

According to an imaging catheter 100 provided in this embodiment, the production process and working principle of the imaging catheter 100 are as follows.

During installation and production, a tubular metal mesh 111 is firstly formed, outside a multi-cavity tube 120, by weaving multi-strand wires; then a single-cavity tube made of insulating material is sleeved outside the metal mesh 111, and at the same time, a lead 114 is pre-embedded and electrically connected with the distal end of the metal mesh 111. Next, the single-cavity catheter is melted by means of hot-melting and then solidified to thermoform an insulating tube 113. The metal mesh 111 is wrapped by the insulating tube 113, so as to form a metal wire tube 110. The portion of insulating tube 113 disposed at the distal end of the metal wire tube 110 is then peeled off, so that a metal wire forming the distal end of the metal mesh 111 leaks out of the insulating tube 113, so as to form a conductive end 112. Finally, two ends of a retaining ring 140 are sleeved on the metal wire tube 110 and a tip 130, respectively, and the retaining ring 140 is fixedly connected with the tip 130 by laser welding, so that the metal wire tube 110 is fixed connected with the tip 130 by the retaining ring 140. Meantime, the conductive end 112 is covered by the retaining ring 140, which prevents the wire exposed from affecting use and causing damage.

When in use, a photographing assembly 200 is firstly put into an imaging catheter 100, a lens 210 of the photographing assembly 200 is held in a photographing hole 134 of the tip 130, and a transmission line 220 of the photographing assembly 200 extends, along a photographing channel 121 of the multi-cavity tube 120, to a handle 300 and is connected with a display device. The imaging catheter 100 equipped with the photographing assembly 200 is then extended into the human body through an endoscopic channel to the desired observation position, so that the desired picture is acquired by the photographing assembly 200 and is imaged on the display device. In the process of observation and use, the static electricity at the tip 130 is led out, through a conductive path formed by connecting the retaining ring 140, the conductive end 112, the metal wire in the insulating tube 113, and the lead 114 in sequence, into the handle 300 for grounding, so as to lead out the static electricity, thereby preventing the operation of the camera component 200 from being affected by static electricity.

The imaging catheter 100 provided by this embodiment has at least the following advantages.

Embodiments of the present disclosure provide an imaging catheter 100, which uses the metal wire wrapped outside the multi-cavity tube 120 as a conductive medium to lead out the static electricity, so as to prevent the imaged picture from being affected by static electricity, to reduce the harm of static electricity to the human body; at the same time, to effectively save the space of the imaging catheter 100, as a result, the overall structure of the imaging catheter 100 is less affected. The metal wire tube 110 is connected with the tip 130 by the retaining ring 140, the metal wire exposed may be wrapped with the annular retaining ring 140, so as to prevent the human body injury caused by a sharp structure formed by the wire in use. At the same time, the conductive end 112 is electrically connected with the tip 130 through the retaining ring 140, so that all metal wires forming the conductive end 112 may be used for grounding, with a good effect of grounding.

This embodiment also provides an imaging device 10 including the above imaging catheter 100. Since the imaging device 10 includes the above imaging catheter 100, the imaging device 10 also has the beneficial effects of preventing the imaged picture from being affected by static electricity, saving space, avoiding damage to the human body, and having a good effect of grounding.

The above are merely specific implementations of the present disclosure, but the scope of protection of the present disclosure is not limited thereto. Any modification or substitution that can be easily conceived by those skilled in the art within the technical scope disclosed in the present disclosure should be covered by the scope of protection of the present disclosure. Therefore, the scope of protection of the present disclosure should be subject to the scope of protection of the claims.

What is claimed is:

1. An imaging catheter, comprising:
a metal wire tube, a tip and a retaining ring;
wherein a metal wire is exposed at one end of the metal wire tube to form a conductive end; and
the retaining ring wrapping the conductive end is connected to the tip to make the conductive end electrically connected with the tip;
the metal wire tube has an export end electrically connected with the conductive end and configured to be grounded,
wherein the metal wire tube further comprises a lead, one end of the lead being electrically connected with the conductive end and the other end of the lead being configured to be grounded to form the export end.

2. The imaging catheter according to claim 1, wherein the conductive end is electrically connected with the tip through the retaining ring.

3. The imaging catheter according to claim 2, wherein a distal end of the conductive end comprises a plurality of metal wire tips arranged in sequence along a circumferential direction of the metal wire tube, and the plurality of metal wire tips are all electrically connected with the retaining ring.

4. The imaging catheter according to claim 1, wherein the conductive end is in contact with the tip, so as to make the conductive end electrically connected with the tip.

5. The imaging catheter according to claim 1, wherein the metal wire tube and the tip are arranged side by side, and the retaining ring is sleeved at a proximal end of the tip.

6. The imaging catheter according to claim 5, wherein an outer wall of the tip comprises a first peripheral surface and a second peripheral surface that are arranged in sequence along an axial direction of the tip, and a radial dimension of the first peripheral surface is smaller than that of the second peripheral surface; and
an inner wall of the retaining ring is matched with the first peripheral surface.

7. The imaging catheter according to claim 6, wherein the outer wall further comprises a stepped surface, two ends of the stepped surface are respectively connected with the first peripheral surface and the second peripheral surface, and the stepped surface is configured to limit a distal end of the retaining ring.

8. The imaging catheter according to claim 7, wherein the stepped surface is disposed along a radial direction of the tip.

9. The imaging catheter according to claim 1, wherein the metal wire tube comprises an insulating tube and the metal wire; part of the metal wire is located inside the insulating tube and part of the metal wire protrudes beyond a distal end of the insulating tube to form the conductive end.

10. The imaging catheter according to claim 9, wherein the insulating tube is thermoformed on the metal wire, so as to cover part of the metal wire.

11. The imaging catheter according to claim 9, wherein the insulating tube is sleeved on a proximal end of the retaining ring.

12. The imaging catheter according to claim 1, wherein the imaging catheter further comprises a multi-cavity tube, which is sleeved with the metal wire tube.

13. The imaging catheter according to claim 12, wherein the multi-cavity tube has a one-piece structure.

14. An imaging device, wherein the imaging device comprises a photographing assembly and the imaging catheter according to claim 1, the photographing assembly being mounted in the tip of the imaging catheter.

* * * * *